US00PP30412P2

(12) United States Plant Patent
Holtmaat

(10) Patent No.: US PP30,412 P2
(45) Date of Patent: Apr. 16, 2019

(54) ***HEUCHERA* PLANT NAMED 'REX PEPPERMINT'**

(50) Latin Name: ***Heuchera* hybrid X *Heuchera sanguinea***
Varietal Denomination: Rex Peppermint

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/732,940

(22) Filed: Jan. 12, 2018

(51) Int. Cl.
*A01H 5/00* (2018.01)

(52) U.S. Cl.
USPC ..... Plt./440

(58) Field of Classification Search
USPC ..... Plt./440
See application file for complete search history.

(56) References Cited

PUBLICATIONS

PLUTO Plant Variety Database Nov. 3, 2018.*

* cited by examiner

*Primary Examiner* — Annette H Para
(74) *Attorney, Agent, or Firm* — C. A. Whealy

(57) ABSTRACT

A new and distinct cultivar of *Heuchera* plant named 'Rex Peppermint', characterized by its uniformly mounded plant habit; densely foliated and bushy appearance; greyed green-colored leaves; long flowering period; numerous inflorescences with sterile red purple-colored flowers; relative low sensitivity to Powdery Mildew; and good garden performance.

2 Drawing Sheets

Botanical designation: *Heuchera* hybrid X *Heuchera sanguinea*.
Cultivar denomination: 'REX PEPPERMINT'.

BACKGROUND OF THE INVENTION

The present invention relates to a new and distinct *Heuchera* plant of *Heuchera*, botanically known as *Heuchera* hybrid X *Heuchera sanguinea* and hereinafter referred to by the name 'Rex Peppermint'.

The objective of the breeding program is to create new compact *Heuchera* plants with attractive leaf colors, less sensitivity to Powdery Mildew and good garden performance.

The new *Heuchera* plant originated from a cross-pollination in August, 2014 in Zuidwolde, The Netherlands of *Heuchera* hybrid 'Electric Lime', disclosed in U.S. Plant Pat. No. 21,872, as the female, or seed, parent with a proprietary selection of *Heuchera sanguinea* identified as code number 083-C063, not patented, as the male, or pollen, parent. The new *Heuchera* plant was discovered and selected by the Inventor as a single flowering plant from within the progeny of the stated cross-pollination in a controlled greenhouse environment in Zuidwolde, The Netherlands in June, 2015.

Asexual reproduction of the new *Heuchera* plant by in vitro meristem culture in a controlled environment in Zuidwolde, The Netherlands since February, 2017 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Rex Peppermint'. These characteristics in combination distinguish 'Rex Peppermint' as a new and distinct *Heuchera* plant:

1. Uniformly mounded plant habit.
2. Densely foliated and bushy appearance.
3. Greyed green-colored leaves.
4. Long flowering period.
5. Numerous inflorescences with sterile red purple-colored flowers.
6. Relative low sensitivity to Powdery Mildew.
7. Good garden performance.

Plants of the new *Heuchera* differ from plants of the female parent, 'Electric Lime', in leaf color as plants of 'Electric Lime' have gold to lime-colored leaves. In addition, plants of the new *Heuchera* and 'Electric Lime' differ in flower color as plants of 'Electric Lime' have white-colored flowers.

Plants of the new *Heuchera* differ from plants of the male parent selection in flower color as plants of the male parent selection have red-colored flowers. In addition, plants of the new *Heuchera* have larger leaves than plants of the male parent selection.

Plants of the new *Heuchera* can be compared to plants of *Heuchera* hybrid 'Berry Timeless', disclosed in U.S. Plant Pat. No. 26,357. In side-by-side comparisons, plants of the new *Heuchera* differ primarily from plants of 'Berry Timeless' in flower sterility as plants of 'Berry Timeless' have fertile flowers than produce fruits and seeds. In addition, plants of the new *Heuchera* and 'Berry Timeless' differ in flower color as plants of 'Berry Timeless' have light pink-colored flowers.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph on the first sheet is a side perspective view of a typical flowering plant of 'Rex Peppermint' grown in a container.

The photograph at the top of the second sheet is a close-up view of typical inflorescences of 'Rex Peppermint'.

The photograph at the bottom of the second sheet is a close-up view of typical leaves of 'Rex Peppermint'.

DETAILED BOTANICAL DESCRIPTION

The aforementioned photographs and following observations, measurements and values describe plants grown during the late spring and early summer in 2-liter containers in an outdoor nursery in Wieringerwerf, The Netherlands and under cultural practices typical of commercial *Heuchera* production. During the production of the plants, day temperatures ranged from 18° C. to 30° C. and night temperatures ranged from 6° C. to 18° C. Plants were one year old when the photographs and the description were taken. In the description, color references are made to The Royal Horticultural Society Colour Chart, 2015 Edition, except where general terms of ordinary dictionary significance are used.

Botanical classification: *Heuchera* hybrid X *Heuchera sanguinea* 'Rex Peppermint'.

Parentage:

- *Female, or seed, parent.*—*Heuchera* hybrid 'Electric Lime', disclosed in U.S. Plant Pat. No. 21,872.
- *Male, or pollen, parent.*—Proprietary selection of *Heuchera sanguinea* identified as code number 083-C063, not patented.

Propagation:

- *Type.*—By in vitro meristem culture.
- *Time to initiate roots, summer.*—About 15 days at temperatures about 20° C.
- *Time to produce a rooted young plant, summer.*—About two months at temperatures about 20° C.
- *Root description.*—Medium in thickness, fibrous; typically creamy white in color, actual color of the roots is dependent on substrate composition, water quality, fertilizer type and formulation, substrate temperature and physiological age of roots.
- *Rooting habit.*—Moderately freely branching; medium density.

Plant description:

- *Plant and growth habit.*—Herbaceous perennial; basal rosette plant habit with leaves developing from the base; densely foliated and dense and bushy appearance; mounded plant habit; moderately vigorous growth habit; low to moderate growth rate.
- *Plant height, soil level to top of foliar plane.*—About 29 cm.
- *Plant height, soil level to top of inflorescences.*—About 61.2 cm.
- *Plant diameter or spread.*—About 62 cm.

Leaf description:

- *Arrangement.*—Alternate in basal rosettes; simple.
- *Length.*—About 15.3 cm.
- *Width.*—About 13.7 cm.
- *Shape.*—Overall, close to orbicular; palmately lobed.
- *Apex.*—Short and abruptly acute.
- *Base.*—Hastate, lobes free, occasionally imbricate.
- *Margin.*—Crenate with about seven lobes; sinuses shallow and divergent.
- *Texture and luster, upper surface.*—Sparsely pubescent; matte.
- *Texture and luster, lower surface.*—Pubescent; slightly glossy.
- *Venation pattern.*—Palmate; reticulate.
- *Color.*—Developing leaves, upper surface: Close to 138B; venation, close to 143A. Developing leaves, lower surface: Close to between 143C and 144A; venation, close to 145B. Fully expanded leaves, upper surface: Close to 189A; venation, close to 139A. Fully expanded leaves, lower surface: Close to between 138B and 147B; venation, close to 145B.
- *Petioles.*—Length: About 16 cm. Diameter: About 3 mm. Strength: Low, flexible. Texture and luster, upper and lower surfaces: Densely pubescent; glossy. Color, upper surface: Darker than 146A. Color, lower surface: Close to 146B.

Flower description:

- *Flower type and flowering habit.*—Single campanulate flowers arranged on compound spikes; each spike with about 180 flowers; about 10,000 flowers develop per plant during the flowering season; flowers face mostly outward to slightly nodding.
- *Fragrance.*—None detected.
- *Time of flowering.*—Plants flower continuously from the spring into the autumn in The Netherlands; plants begin flowering about four months after planting.
- *Inflorescence longevity.*—Individual flowers last a few weeks on the plant; flowers not persistent.
- *Inflorescence length.*—About 29.8 cm.
- *Inflorescence width.*—About 8.2 cm.
- *Flower diameter.*—About 5 mm.
- *Flower depth (height).*—About 6 mm.
- *Flower buds.*—Height: About 4 mm. Diameter: About 1.75 mm. Shape: Oblong. Texture and luster: Densely pubescent; matte. Color: Close to 53C and 53D.
- *Petals.*—Quantity and arrangement: Five petals in a single whorl. Length: About 3 mm. Width: About 0.5 mm. Shape: Oblanceolate. Apex: Acute. Base: Narrowly attenuate. Margin: Entire. Texture and luster, upper and lower surfaces: Smooth, glabrous; matte. Color: When opening, upper and lower surfaces: Close to 62B. Fully opened, upper and lower surfaces: Close to 62C; color does not change with development.
- *Sepals.*—Quantity and arrangement: Five sepals in a single whorl; fused at base. Length: About 6 mm. Width: About 1.5 mm. Shape: Broadly oblong. Apex: Broadly acute. Margin: Entire. Texture and luster, upper and lower surfaces: Densely pubescent; matte. Color: When opening, upper surface: Close to 67C to 67D. When opening, lower surface: Close to 61C.

Fully opened, upper surface: Close to 68D. Fully opened, lower surface: Close to 61D.

*Peduncles*.—Length: About 48.2 cm. Diameter: About 2.5 mm. Strength: Moderately strong. Aspect: About 10° from vertical. Texture and luster: Densely pubescent; moderately glossy. Color: Close to 146A to darker than 146A.

*Pedicels*.—Length: About 2 mm. Diameter: About 0.5 mm. Strength: Moderately strong. Aspect: About 30° from peduncle axis. Texture and luster: Densely pubescent; matte. Color: Close to 183A.

*Reproductive organs*.—Androecium: Stamen number: Five per flower. Filament length: About 3 mm. Filament color: Close to between N155B and NN155D. Anther length: About 0.5 mm. Anther shape: Deltoid. Anther color: Close to 160D. Amount of pollen: Scarce. Pollen color: Close to 156D. Gynoecium: Pistil number: Two per flower. Pistil length: About 3 mm. Style length: About 2.75 mm. Style color: Close to NN155D. Stigma diameter: About 0.2 mm. Stigma shape: Club-shaped. Stigma color: Close to NN155D. Ovary color: Close to 150D.

*Seeds and fruits*.—Flowers of plants of the new *Heuchera* are sterile. Seed and fruit development have not been observed on plants of the new *Heuchera* to date.

Pathogen & pest resistance: Plants of the new *Heuchera* have been observed to be relatively less sensitive to Powdery Mildew (*Sphaerotheca macularis*). Resistance to pests and other pathogens has not been observed on plants of the new *Heuchera* grown under commercial conditions to date.

Garden performance: Plants of the new *Heuchera* have been observed to have good garden performance and to tolerate high temperatures about 35° C. and to be suitable for USDA Hardiness Zones 3 through 9.

It is claimed:

1. A new and distinct *Heuchera* plant named 'Rex Peppermint' as illustrated and described.

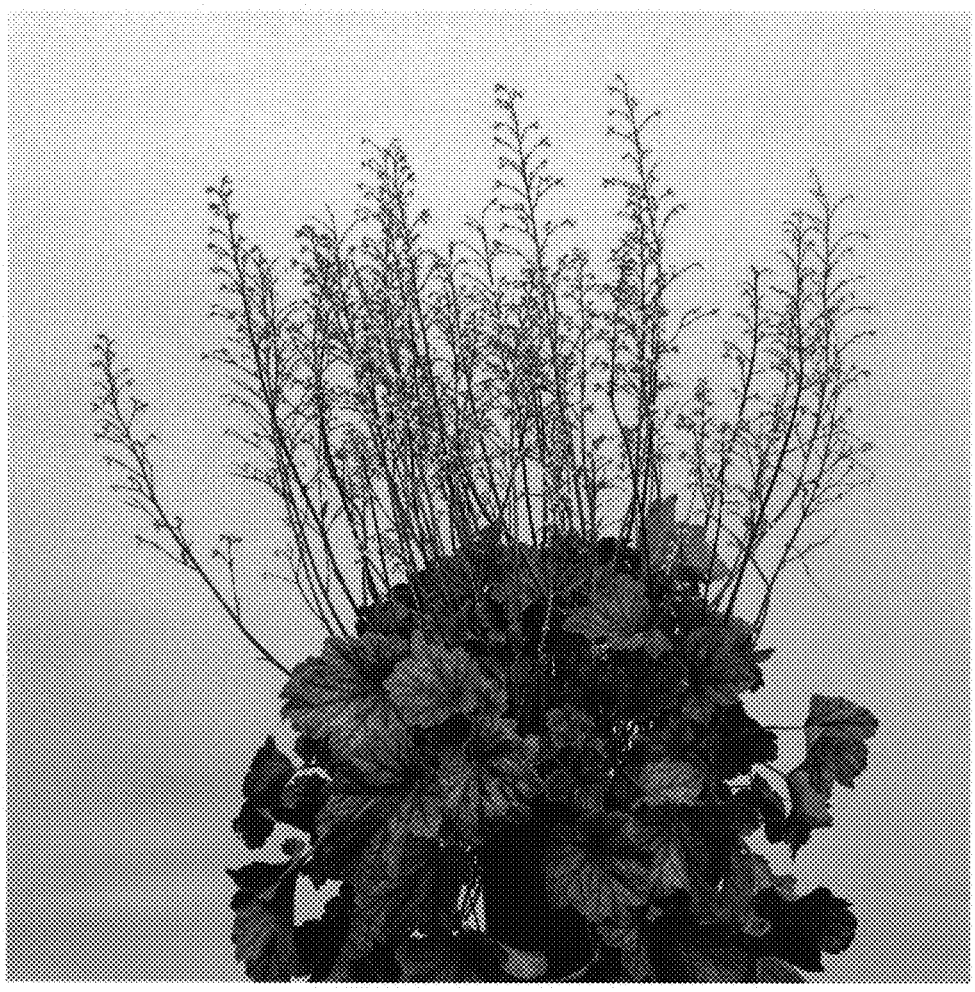

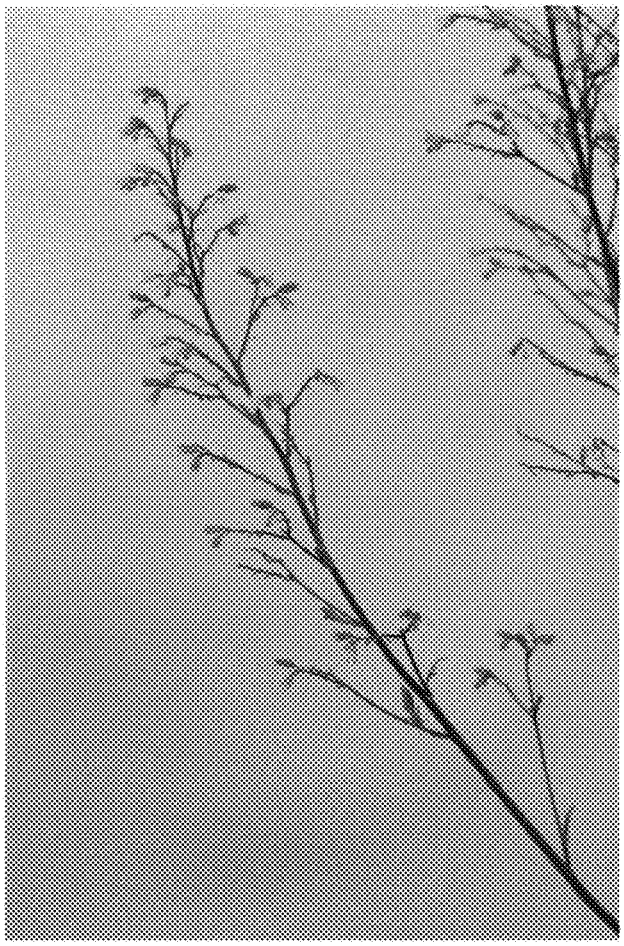
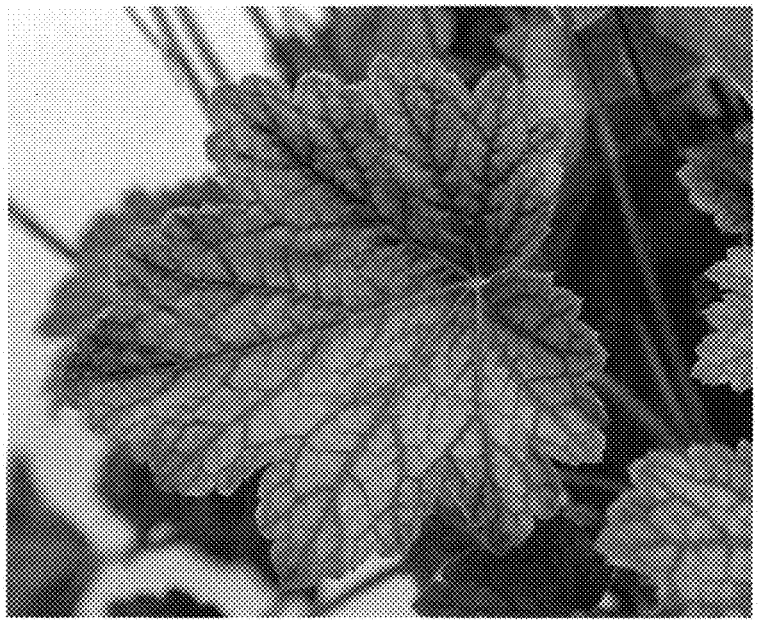

* * * * *